United States Patent
Yangdai

(10) Patent No.: US 11,538,151 B2
(45) Date of Patent: Dec. 27, 2022

(54) METHOD FOR MEASURING OBJECTS IN DIGESTIVE TRACT BASED ON IMAGING SYSTEM

(71) Applicant: ANKON TECHNOLOGIES CO., LTD, Wuhan (CN)

(72) Inventor: Tianyi Yangdai, Wuhan (CN)

(73) Assignee: ANKON TECHNOLOGIES CO., LTD, Wuhan (CN)

(*) Notice: Subject to any disclaimer, the term of this patent is extended or adjusted under 35 U.S.C. 154(b) by 235 days.

(21) Appl. No.: 16/859,772

(22) Filed: Apr. 27, 2020

(65) Prior Publication Data

US 2020/0342596 A1    Oct. 29, 2020

(30) Foreign Application Priority Data

Apr. 28, 2019 (CN) .................. 201910347967.X

(51) Int. Cl.
- *G06T 7/00* (2017.01)
- *G06T 7/80* (2017.01)
- *A61B 1/04* (2006.01)

(52) U.S. Cl.
CPC .............. *G06T 7/0012* (2013.01); *G06T 7/80* (2017.01); *A61B 1/041* (2013.01); *G06T 2207/10028* (2013.01); *G06T 2207/20088* (2013.01); *G06T 2207/30092* (2013.01)

(58) Field of Classification Search
CPC ............ G06T 7/0012; G06T 7/80; G06T 2207/10028; G06T 2207/20088; G06T 2207/30092; G06T 7/50; G06T 2207/10068; G06T 2207/30028; A61B 1/041; A61B 5/1076; A61B 5/1079
See application file for complete search history.

(56) References Cited

U.S. PATENT DOCUMENTS

| | | | | |
|---|---|---|---|---|
| 11,074,721 | B2* | 7/2021 | Yangdai | G06T 7/62 |
| 2012/0253122 | A1* | 10/2012 | Minetoma | A61B 1/0638 600/109 |
| 2013/0271585 | A1* | 10/2013 | Khan | H04N 9/0451 348/222.1 |
| 2016/0113480 | A1* | 4/2016 | Homan | H04N 19/89 348/65 |
| 2019/0365213 | A1* | 12/2019 | Park | A61B 1/00193 |

* cited by examiner

*Primary Examiner* — Molly Wilburn
(74) *Attorney, Agent, or Firm* — Treasure IP Group, LLC

(57) ABSTRACT

A method for measuring objects in a digestive tract based on an imaging system is provided. The imaging system captures a detection image in the measurement stage. The depth distance $z_i$ from a target point P' to a board is calculated, a correction factor is obtained according to the predicted brightness $g^{-1}(z_i)$ of a reference point P in the detection image. The depth image $z(x, y)$ from the actual position of each pixel to the board is calibrated by the correction factor. The scale r of each pixel is calculated according to the depth image $z(x, y)$. The actual two-dimensional coordinates $S_i'$ of each pixel are calculated by the scale r, and the actual three-dimensional coordinates $(S_i', z(x, y))$ of each pixel are obtained. The distance between any two pixels in the detection image or the area within any range are calculated.

11 Claims, 4 Drawing Sheets

METHOD FOR MEASURING OBJECTS IN DIGESTIVE TRACT BASED ON IMAGING SYSTEM

CROSS-REFERENCE OF RELATED APPLICATIONS

The application claims priority to Chinese Patent Application No. 201910347967.X filed on Apr. 28, 2019, the contents of which are incorporated by reference herein.

FIELD OF INVENTION

The present invention relates to image processing, and more particularly to a method for measuring objects in digestive tract based on an imaging system.

BACKGROUND

At present, capsule endoscopes have become increasingly popular for digestive tract examination. Doctors examine subjects through images taken by the capsule endoscopes inside the digestive tract of the subjects. However, for a normal capsule endoscope, when a captured image shows a lesion, the doctor can only determine through the shape, color, position and other characteristics of the lesion, but cannot obtain the size information of the lesion, and therefore cannot give an accurate quantitative analysis result.

In the prior art, for example, according to a Chinese Patent No. CN107072498A, a method for distance measuring in the digestive tract is provided. In the above method, some distance measuring pixels are distributed in a common image sensor to generate distance measuring data for object depth information, that is depth image. Then, the distance measuring data of known pixel positions is used to interpolate the depth of the pixel position of the distance measuring data not derived in the depth image. In the above method, the calculation method is complicated, and the requirements on components are high. The distance measuring pixels need to be evenly distributed in the image sensor, and more measurement points are required. If there are a plurality of measurement points, a large deviation can appear in subsequent gradient calculations, which can eventually cause measurement distortion.

According to a Chinese Patent No. CN101902961A, a device, system and method for estimating the size of an object in a body lumen is provided. In the above method, a laser device is configured in the capsule endoscope, and distance measurement and object measurement are performed by laser points and image brightness. However, the effect of media in the digestive tract is ignored in the method. The environment of the digestive tract is complex. Both air and digestive fluid can affect the optical path of laser and directly affect the result of laser distance measuring. In addition, the distance measurement can always depend on the results of laser distance measuring. Each measurement requires laser distance measuring, and a plurality of calculations are required at each time of measurement, which consumes manpower and material resources.

Furthermore, in the prior art as described above, the size is measured with the aid of additional device, such as a time of flight (ToF) distance-measuring chip, which undoubtedly increases the cost and complexity of measuring system.

Therefore, it is necessary to design a new method for measuring objects in the digestive tract with more convenient calculation steps.

SUMMARY OF THE INVENTION

To solve one of the above problems, the present invention provides a method for measuring objects in digestive tract based on an imaging system, comprising: simulating an environment in the digestive tract and entering a calibration stage of the imaging system;

setting a plurality of calibration points $Q'$ on a transparent enclosure of the imaging system;

controlling a photographing unit of the imaging system to photograph and form a calibration image, and recording the calibration point $Q'$ imaged in the calibration image as an imaging point $Q$;

calculating and determining the relationship between the relative angle $\theta$ of the calibration point $Q$ relative to the optical axis of the photographing unit and the pixel distance $\Delta q'$ from the imaging point $Q$ to the center of the calibration image, and recording it as:

$$\theta = f(\Delta q') \quad (1);$$

calculating and determining the relationship between the brightness $\varphi$ of any pixel in the calibration image and the depth distance $z$ from the actual position of the pixel in the simulated digestive tract to a board where the photographing unit is disposed, and recording it as:

$$z(x,y) = g(\varphi(x,y)) \quad (2);$$

calculating the relationship between the scale $r$ of any pixel in the calibration image and the depth distance $z$ from the actual position of the pixel in the simulated digestive tract to the board where the photographing unit is disposed, where scale is the actual length represented by unit pixel in the image, and recording it as:

$$r = dz \quad (3);$$

entering a measurement stage after calibration is completed;

placing the imaging system in the digestive tract;

capturing and obtaining a detection image;

determining a region in the detection image where the transparent enclosure contacts with the digestive tract wall, and recording it as a contact region, and setting at least one reference point $P$ in the contact region, and recording the actual position of the reference point in the digestive tract as a target point $P'$;

calculating the pixel distance $\Delta p$ from the reference point $P$ to the center of the detection image separately, and putting it into equation 1 to obtain the relative angle $\theta$ of the target point $P'$ relative to the optical axis of the photographing unit;

calculating the actual distance from the target point $P'$ to the board separately and recording it as depth distance $z_i$;

obtaining the predicted brightness $g^{-1}(z_i)$ of the reference point $P$ in the detection image according to equation 2 and the depth distance $z_i$;

comparing the predicted brightness $g^{-1}(z_i)$ of the reference point $P$ with the actual pixel brightness $img(P_i)$ of the reference point $P$ to obtain a correction factor $k_i$, and recording it as:

$$k_i = \frac{g^{-1}(z_i)}{img(P_i)}; \quad (4)$$

obtaining a mean value $\bar{k}$ of the correction factors $k_i$ of all reference points $P$;

calibrating all pixels in the detection image with the mean value $\bar{k}$ of the correction factors to obtain the depth distance from the actual position of each pixel in the digestive tract to the board, and recording it as depth image z(x, y), where:

$$z(x,y)=g(\overline{k}\text{img}(x,y)) \quad (5);$$

calculating the scale r of each pixel in the detection image according to equation 3 and the depth image z(x, y);

obtaining the pixel coordinates $S_i$ of each pixel point in the detection image, and calculating the actual two-dimensional coordinates $S_i'$ of each pixel in the detection image by the scale r;

integrating to obtain the actual three-dimensional coordinates $(S_i', z(x, y))$ of each pixel;

calculating or measuring the distance between any two pixels in the detection image or the area within any range.

In an embodiment, the step "determining the region in the detection image where the transparent enclosure contacts with the digestive tract wall" comprises: selecting the edge part of the detection image away from the center of the detection image;

obtaining the brightness T of each pixel in the edge part;

gathering the pixels in a region which the brightness T is greater than a threshold τ as the contact region.

In an embodiment, the step "selecting the edge part of the detection image away from the center of the detection image" comprises:

marking an inner ring on the detection image that is centered on the center of the detection image, wherein the inner ring is close to the edge of the detection image and does not intersect;

marking an outer ring on the detection image that is centered on the center of the detection image, wherein the outer ring intersects with the edge of the detection image;

recording the part enclosed by the inner ring, the outer ring, and the image edge as the edge part.

In an embodiment, the digestive tract comprises a plurality of regions and the imaging system comprises a plurality of exposure levels, and wherein, after the step "obtaining the mean value $\overline{k}$ of the correction factors $k_i$ of all reference points P", the correction factors are stored according to different exposure levels and different digestive tract regions.

In an embodiment, after two or more mean values $\overline{k}$ of correction factors are obtained at the same exposure level and digestive tract region, the average of the mean values $\overline{k}$ of correction factors is calculated before storing and updating.

In an embodiment, the step "calculating the actual distance from the target point P' to the board separately and recording it as depth distance $z_i$ of the reference point P" comprises:

obtaining the radius R of a front enclosure of the transparent enclosure; calculating the distance R cos θ from the target point P' to the spherical center of the front enclosure separately;

obtaining the axial length H of an annular enclosure of the transparent enclosure; calculating the depth distance $z_i$=R cos θ+H from the target point P' to the board separately.

In an embodiment, the step "obtaining the depth distance from the actual position of each pixel in the digestive tract to the board" or "integrating to obtain the actual three-dimensional coordinates $(S_i',z(x,y))$ of each pixel" further comprises:

determining the value of the depth distance z of each pixel;

when $t_1 \leq z \leq t_2$, it is determined that the pixel is within the effective section of the detection image;

when $z<t_1$ or $z>t_2$, it is determined that the pixel is within the ineffective section of the detection image.

In an embodiment, the step "calculating or measuring the distance between any two pixels in the detection image or the area within any range" is followed by:

calculating a straight-line distance between any two pixels selected by a user in the effective section according to the three-dimensional coordinates of the two pixels; or, building a three-dimensional image of any area according to the three-dimensional coordinates of pixels in the area selected by a user in the effective section, and calculating a straight-line distance between any two pixels selected by the user from the three-dimensional image; or, calculating the area of any region selected by a user in the effective section according to the three-dimensional coordinates of the region; or, forming a scale in the effective section, and marking graduations on the scale as those of actual length; or, identifying the lesion region in the effective section automatically, and calculating the size or area of the region.

In an embodiment, $t_1$=0, and $t_2$=60 mm.

In an embodiment, the step "capturing and obtaining a detection image" comprises:

controlling the imaging system to capture and obtain an image;

correcting the radial distortion of the captured image and forming a detection image, and recording it as:

$$\text{img\_out}(x,y)=\text{img\_in}(x(1+l_1R^2+l_2R^4),y(1+l_1R^2+l_2R^4)) \quad (6);$$

where, $R=\sqrt{x^2+y^2}$ represents the pixel distance from the pixel to the center of the detection image, $l_1$ and $l_2$ represent distortion parameters of the imaging system, x represents x-coordinate of the pixel, y represents y-coordinate of the pixel, img_in represents input image, and img_out represent corrected image.

The present invention further provides a measuring system for objects in digestive tract based on an imaging system, comprising:

an identification module, configured to identify a contact region and a reference point P;

a calibration calculation module, configured to calculate the relationship between the relative angle θ of a calibration point Q' relative to the optical axis of a photographing unit of the imaging system and the pixel distance Δq' from an imaging point Q to the center of a calibration image and record as equation 1, and to calculate the relationship between the brightness φ of any pixel in the calibration image and the depth distance z from the actual position of the pixel in a simulated digestive tract to the imaging system, and record it as equation 2, and to calculate and determine the relationship between the scale r of any pixel in the calibration image and the depth distance z from the actual position of the pixel in the simulated digestive tract to the imaging system, and record it as equation 3;

a brightness detection module, configured to identify the brightness of any pixel or all pixels in the calibration image or a detection image;

a measurement calculation module, configured to obtain the equation 1 and the pixel distance Δp from the reference point P to the center of the detection image to calculate the relative angle θ of a target point P' relative to the optical axis of the photographing unit, and to calculate actual distance from the target point P' to a board where the photographing unit is disposed and record it as depth distance $z_i$, and to obtain the depth distance $z_i$, the equation 2 and the actual pixel brightness of the reference point P to calculate a correction factor $k_i$, and to obtain the equation 2 to calculate and obtain the depth distance z(x, y) from the actual position of each pixel in the digestive tract to the board, and to obtain the equation 3 to calculate the actual two-dimensional coordinates $S_i$, and integrate to obtain the actual three-dimensional coordinates of ($S_i'$, z (x, y)) of each pixel.

Compared to the prior art, the method for measuring objects in the digestive tract based on the imaging system in the present invention can obtain some parameter information in advance through the calibration stage of the imaging system, and thereby facilitate the calculation in the measurement stage and avoid calculation error caused by equipment difference between imaging systems. Moreover, by determining the contact region, the reference point in the captured image can directly correspond to the target point on the transparent enclosure of the imaging system, so that no other hardware is needed to measure the depth distance $z_i$ for reference point, making the components simpler and the calculation steps more concise.

DETAILED DESCRIPTION

Figure 1:
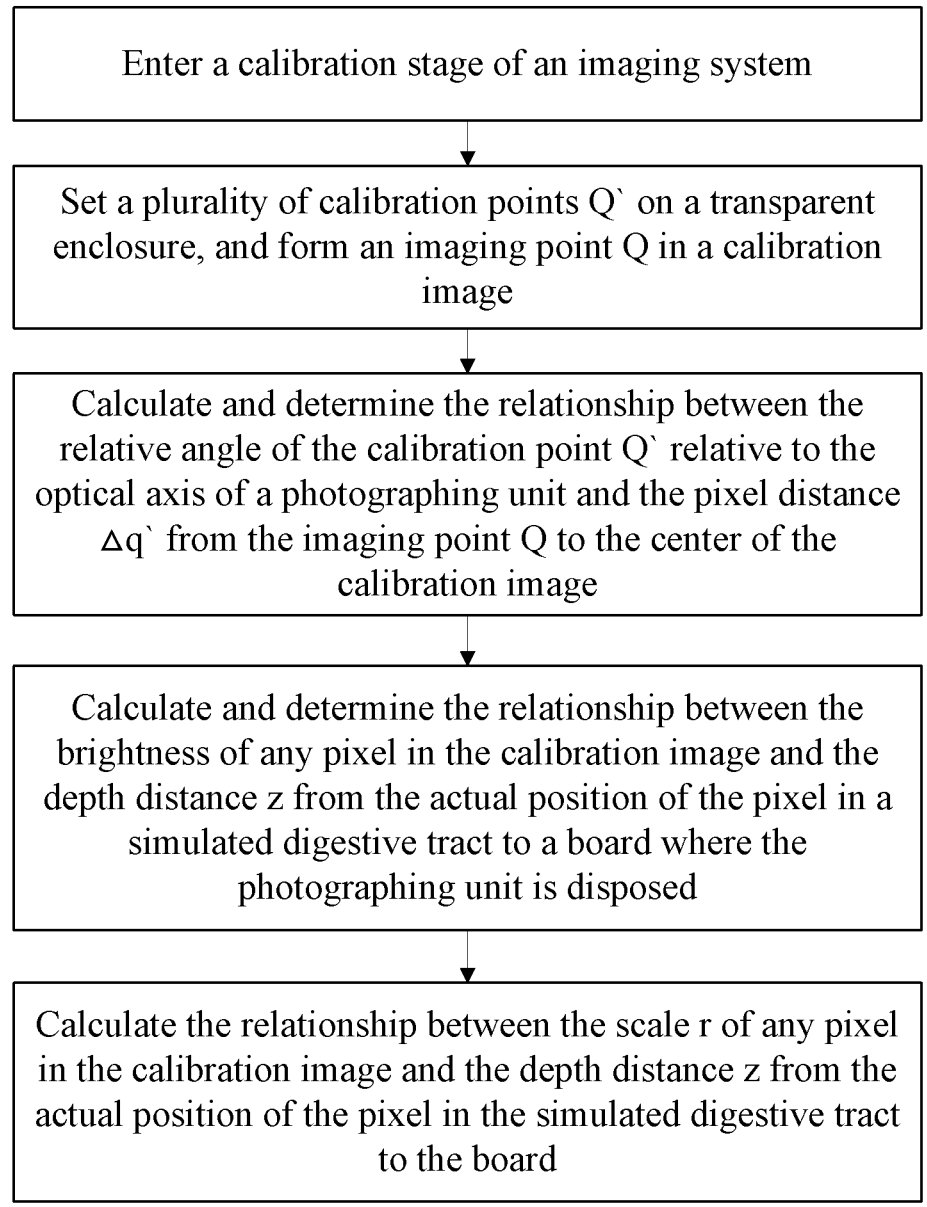
FIG. 1 shows an exemplary flowchart of the measurement method in a calibration stage of the present invention.
Figure 2:
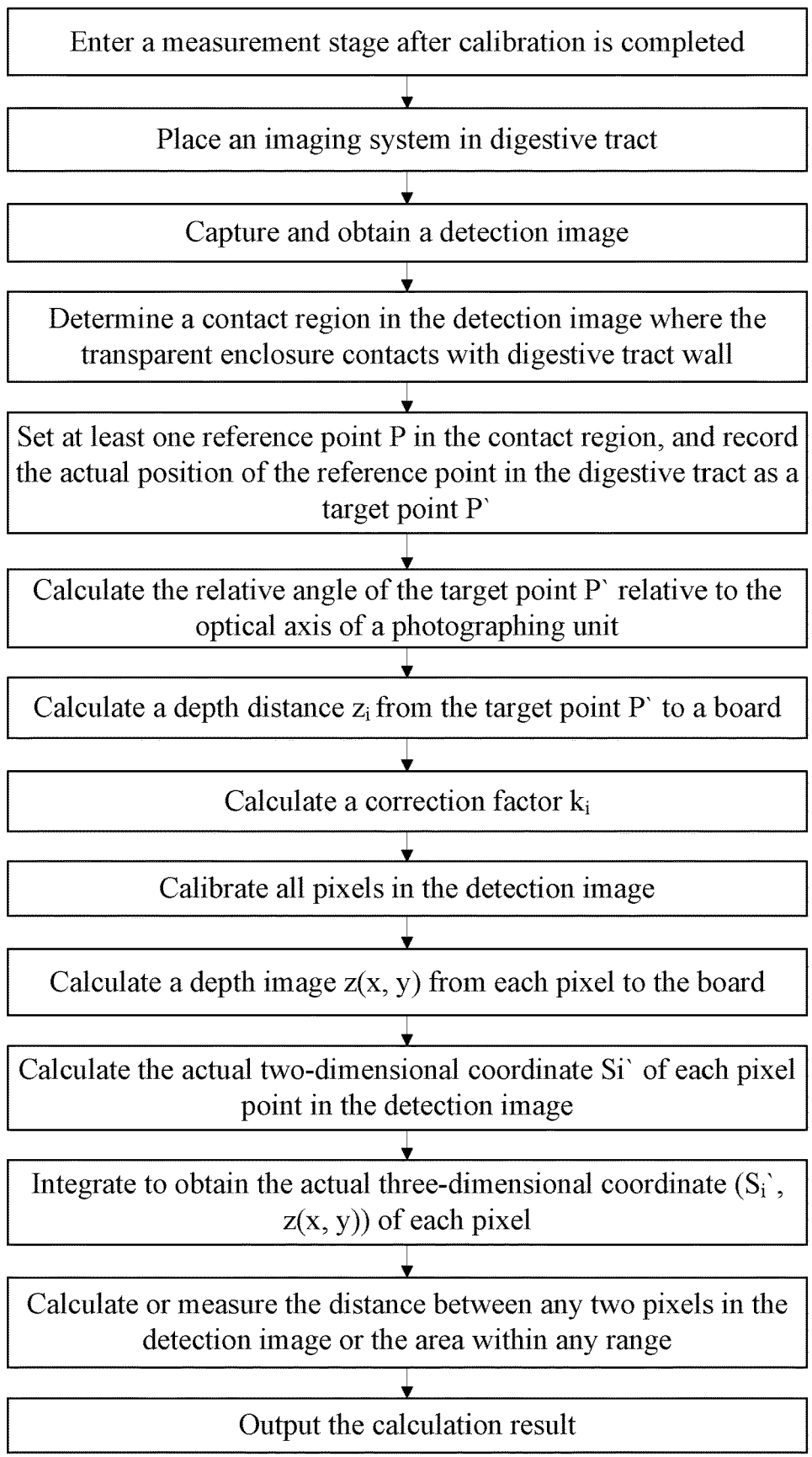
FIG. 2 shows an exemplary flowchart of the measurement method in a measurement stage of the present invention.

In order to enable those skilled in the art to better understand the technical solutions disclosed, the present invention can be described in detail below with reference to the accompanying drawings and preferred embodiments. However, the embodiments are not intended to limit the invention, and obviously, the described embodiments are only a part of the embodiments of the present invention, but not all of them. All other embodiments obtained by those having ordinary skill in the art without creative work based on the embodiments of the present invention are included in the scope of the present invention.

Referring to FIGS. 1-4, the present invention provides a method for measuring objects in digestive tract based on an imaging system and one or more computer processors, where the imaging system can be introduced into the digestive tract to take images of the objects therein, and a two-axis coordinate system is preset on the images taken by the imaging system to determine the coordinates of any pixel in the image. In the embodiment, the imaging system is a capsule endoscope. The capsule endoscope comprises a board 104, a photographing unit 102 disposed on the board 104, and a transparent enclosure disposed around the photographing unit 102. The photographing unit 102 can take images through the transparent enclosure. If the imaging system is other equipment, as long as the components are included, the object of the present invention can also be achieved.

Moreover, since the imaging system, especially the capsule endoscope in the embodiment, is in the digestive tract, the transparent enclosure generally comes into contact with the inner wall of the digestive tract. Especially in esophagus and large intestine, the lumen space is small because of insufficient water. During the peristalsis of colon and swallowing of the esophagus, the inner wall of colon and esophagus can wrap and squeeze the capsule endoscope, and the inner wall can usually come into contact with the transparent enclosure. In the small intestine, due to its curved structure, smaller inner diameter, and more frequent contraction, the inner wall can also contact with the transparent enclosure. Therefore, in the esophagus, small intestine, and large intestine, it can be assumed that the inner wall of the digestive tract is in contact with the imaging system, so that the captured image has a part where the transparent enclosure contacts with the digestive tract.

Specifically, the measurement method comprises:

simulating an environment of the digestive tract and entering a calibration stage of the imaging system;

setting a plurality of calibration points Q on the transparent enclosure of the imaging system;

controlling the photographing unit 102 of the imaging system to photograph and form a calibration image, and recording the calibration point Q' imaged in the calibration image as an imaging point Q;

calculating and determining the relationship between the relative angle θ of the calibration point Q' relative to the optical axis of the photographing unit 102 and the pixel distance Δq' from the imaging point Q to the center of the calibration image, and recording it as:

$$\theta = f(\Delta q') \quad (1);$$

calculating and determining the relationship between the brightness φ of any pixel in the calibration image and the depth distance z from the actual position of the pixel in the simulated digestive tract to the board 104 where the photographing unit 102 is disposed, and recording it as:

$$z(x,y) = g(\varphi(x,y)) \quad (2);$$

calculating the relationship between the scale r of any pixel in the calibration image and the depth distance z from the actual position of the pixel in the simulated digestive tract to the board 104 where the photographing unit 102 is disposed, where scale is the actual length represented by unit pixel in the calibration image, and recording it as:

$$r = dz \quad (3);$$

entering a measurement stage after calibration is completed;

placing the imaging system in the digestive tract;

capturing and obtaining a detection image;

determining the region in the detection image where the transparent enclosure contacts with the digestive tract wall, and recording it as a contact region, and setting at least one reference point P in the contact region, and recording the actual position of the reference point in the digestive tract as a target point P';

calculating the pixel distance Δp from the reference point P to the center of the detection image separately, and putting it into equation 1 to obtain the relative angle θ of the target point P' relative to the optical axis of the photographing unit 102;

calculating the actual distance from the target point P' to the board 104 separately and recording it as a depth distance $z_i$;

obtaining the predicted brightness $g^{-1}(z_i)$ of the reference point P in the detection image according to equation 2 and the depth distance $z_i$;

comparing the predicted brightness $g^{-1}(z_i)$ of the reference point P with the actual pixel brightness img($P_i$) of the reference point P to obtain a correction factor $k_i$, and recording it as:

$$k_i = \frac{g^{-1}(z_i)}{\text{img}(P_i)}; \tag{4}$$

obtaining a mean value $\bar{k}$ of the correction factors $k_i$ of all reference points P;

calibrating all pixels in the detection image with the mean value $\bar{k}$ to obtain the depth distance from each pixel to the board 104, and recording it as the depth image z(x, y), where:

$$z(x,y)=g(\bar{k}\text{img}(x,y)) \tag{5};$$

calculating the scale r of each pixel in the detection image according to equation 3 and the depth image z(x, y);

obtaining the pixel coordinates $S_i$ of each pixel point in the detection image, and calculating the actual two-dimensional coordinates $S_i'$ of each pixel in the detection image by the scale r;

integrating to obtain the actual three-dimensional coordinates ($S_i'$, z(x, y)) of each pixel;

calculating or measuring the distance between any two pixels in the detection image or the area within any range.

In the above method, calibration is first performed in the calibration stage. The first step is to obtain the relationship between the relative angle θ of the calibration point Q' relative to the optical axis of the photographing unit 102 and the pixel distance Δq' from the imaging point Q to the center of the calibration image. The second step is to obtain the relationship between the brightness φ of any pixel in the calibration image and the depth distance z from the actual position of the pixel in the simulated digestive tract to the board 104 where the photographing unit 102 is disposed. The third step is to obtain the relationship between the scale r of any pixel in the calibration image and the depth distance z from the actual position of the pixel in the simulated digestive tract to the board. Then, in the actual measurement stage, determining a region in the detection image where the digestive tract is in contact with the transparent enclosure. The target point P' in the contact region is both a point on the transparent enclosure and a point within the digestive tract. Therefore, the relative angle θ of the target point P' relative to the optical axis of the photographing unit 102 can be obtained through the reference point P of the target point P' in the detection image. Then the actual distance from the target point P' to the board 104 can be calculated through the structure of the imaging system, where the actual distance is the depth distance $z_i$. Then the predicted brightness $g^{-1}(z_i)$ of the reference point P can be calculated. Then, the predicted brightness $g^{-1}(z_i)$ of the reference point P is compared with the actual pixel brightness img($P_i$) of the reference point P to obtain the correction factor $k_i$. After obtaining the correction factor $k_i$, all pixels in the detection image are corrected to obtain the predicted brightness of each pixel, so as to obtain the depth distance z(x, y) from each pixel to the imaging system. Finally, the actual two-dimensional coordinates $S_i'$ on the xoy plane of each pixel are obtained through the scale. The information described above is integrated to obtain the actual three-dimensional coordinates ($S_i'$, z(x, y)) of each pixel. Therefore, after knowing the actual three-dimensional coordinates of each pixel, the distance between any two pixels in the detection image or the area within any range can be calculated.

Moreover, assuming that the transparent enclosure is in contact with the digestive tract, the target point P' in the digestive tract is the target point P' on the transparent enclosure, so that the actual coordinates of pixels in the captured image can be directly obtained according to the internal structure of the imaging system, with no need for the structure of other components, and the overall structure of the imaging system is relatively simple.

The actual pixel brightness img($P_i$) of the reference point P is the brightness of the pixel at point P in the detection image. Since the form of function g can be related to the reflection coefficient of the object surface, exposure parameters, media environment, number of LEDs, distribution, camera lens performance of the photographing unit 102 and the response of image sensor of the photographing unit 102, although the relationship between the brightness φ of any pixel in the calibration image and the depth distance z from the actual position of the pixel in the simulated digestive tract to the board where the photographing unit is disposed is obtained during calibration, when the actual distance $z_i$ and the predicted brightness $g^{-1}(z_i)$ are obtained in subsequent process, it still needs to be compared with the actual pixel brightness of the reference point P to obtain a correction factor $k_i$ to correct the actual brightness of other pixels to obtain the depth distance z of said other pixels.

In addition, in the final calculation process, two pixels or any area can be selected manually or by a system, and then measured by the system; or, the system provides a scale, and the values are directly read or measured manually.

Therefore, each imaging system needs to first enter the calibration stage to measure and determine different parameters of the imaging system. Accordingly, even though there is difference between imaging systems, different parameters of the imaging system can be obtained in the process of calibration, and the parameters are needed for measurement and calculation in the subsequent process, so as to avoid errors due to difference in equipment.

It should be noted that, in the embodiment, when the photographing unit 102 takes an image, the optical axis of the photographing unit 102 is through the center of the image, and the connecting line between the optical axis and the center of the image is recorded as a reference line, that is the direction of z axis. Therefore, the depth distance from the reference point P in the image to the imaging system does not refer to a linear distance between the two, but refers to the distance between the two in line with the direction of the reference line. In addition, the image taken by the imaging system is preset with a two-axis coordinate system recorded as a xoy plane coordinate system. The pixel coordinates $S_i$ and the actual two-dimensional coordinates $S_i'$ of each pixel are based on the xoy plane. Then the depth image z (x, y) is obtained, and the two is combined into the three-dimensional coordinates.

First of all, during calibration, the imaging system needs to be placed in a calibration box. The calibration box is a dark chamber and ensures opacity to light. The calibration box comprises a fixing frame for fixing the imaging system, a target board for the imaging system to take images thereon, and the calibration box is also filled with a simulation medium that can be simulated digestive liquid or air. The imaging system can move on the fixing frame. The imaging system further comprises a plurality of LEDs, where the LEDs and the photographing unit 102 are both arranged on the inner board of the capsule endoscope, and the number of the LEDs is set to be 2 to 5, and they are distributed around the photographing unit 102. Therefore, the imaging system can be set to take images at different positions, under different lighting conditions, in different simulation media and on different target boards to obtain the parameter information. The target board can also be replaced, such as a hard board simulating the mucosal surface or imitating the color of mucosa. When the calibration box is used for other calibrations, only the target board needs to be replaced with a whiteboard, a chess board or a line pairs card, so that white balance correction, camera parameter calibration, resolution measurement and other calibrations can be performed. The light field distribution of the LEDs can affect the distribution of the brightness $\varphi$ of any pixel in the calibration image, so each different imaging system must be calibrated separately.

Moreover, during calibration, after each image is obtained, a radial distortion correction for the image is required. This is because the capturing of image can be affected by the distortion parameters of different cameras. Therefore, distortion correction can improve the accuracy of size calculation of objects on the image, especially the measurement of objects at the edge of the image. The image with radial distortion correction can be calibrated to obtain parameter information. The specific information of radial distortion correction can be described in detail later.

In the measurement stage, as the correction factor is obtained, all pixels in the image can be calibrated and the actual depth distance z (x, y) from the actual position of each pixel in the digestive tract to the board 104 can be obtained. Due to different photographing environments of the imaging system and different positions in the digestive tract, the correction factor can be affected accordingly. Specifically, the digestive tract comprises a plurality of regions and the imaging system comprises a plurality of exposure levels according to different photographing environments. So, after the step "obtaining the mean value $\overline{k}$ of the correction factors $k_i$ of all reference points P", the mean value $\overline{k}$ of the correction factors should be stored according to different exposure levels and different digestive tract regions, and updated to a correction factor k. In the same digestive tract region and with the same exposure parameters, the correction factors k have small gap, so even if there is no reference point P, the depth distance z(x, y) from each pixel to the imaging system can also be obtained through a predicted correction factor. This method can not only improve the anti-interference ability of the entire system algorithm, but also reduce the number of images taken with the reference point P, thus improving work efficiency.

If two or more correction factors k are obtained at the same exposure level and in the same digestive tract region, the average of the correction factors k should be calculated before storing and updating. Specifically, as shown in table 1, the digestive tract regions include esophagus, small intestine, large intestine, etc., the exposure levels include 1, 2, . . . to N, and different exposure levels and digestive tract regions are stored with different correction factors k. Therefore, if the reference point P is not obtained to calculate the correction factor k, the corresponding correction factor can also be selected for calculation from the table below according to the exposure level and digestive tract region.

TABLE 1

| Exposure levels | Digestive tract regions | | |
| --- | --- | --- | --- |
| | Esophagus | Small intestine | Large intestine |
| 1 | k11 | k12 | k13 |
| 2 | k21 | k22 | k23 |
| . . . | . . . | . . . | . . . |
| N | kN1 | kN2 | kN3 |

As described above, the premise of the present invention is to assume that the inner wall of the digestive tract is in contact with the transparent enclosure and analyze the target point P' in the contact region. Therefore, how to determine the contact region in the detection image is a difficult point. The step "determining the region in the detection image where the transparent enclosure contacts with the digestive tract wall" comprises:

selecting the edge part of the detection image away from the center of the detection image;

obtaining the brightness T of each pixel in the edge part;

gathering the pixels in a region which the brightness T is greater than a threshold $\tau$ as the contact region.

Obviously, due to the concentrated propagation of light beams emitted from the LEDs of the imaging system and the light reflection on the inner wall of the digestive tract, there is a clear brightness step difference in the images taken by the imaging system. When the target is closer to the transparent enclosure, the brightness of the target in the corresponding image is higher, and when the target is farther from the transparent enclosure, the brightness of the target in the corresponding image is lower.

Therefore, the photographing environments in the digestive tract can be simulated in the early simulation experiment stage to calculate the brightness distribution of the contact region, so as to derive the threshold $\tau$. The region composed of all pixels greater than the threshold $\tau$ can be regarded as the contact region.

In addition, determination of the contact region by the threshold $\tau$ may have an error. For example, omitting some contact points results in a determination with omission, or treating some misjudged points that are not in contact but are closer as contact points results in a misjudgment. But the determination with omission can basically not cause a calculation error. If a misjudgment occurs, the misjudged points that are not actually contacted are determined as contact points, which may cause an error. However, the range of the above error cannot be very large and can be ignored, mainly due to the following three reasons. First, the threshold $\tau$ can be a relatively large value, and under the threshold $\tau$, the above determination is more likely to be a determination with omission but not misjudgment. Second, even if the misjudged points do not contact with the transparent enclosure, they are usually very close to the transparent enclosure, so the above error can be ignored. Third, in the above steps, at least one reference point P can be selected in the contact region, and in the actual operation process, in order to make the mean value $\overline{k}$ of correction factors accurate, a large number of reference points P can be taken, so that the above error can be further reduced after averaging.

Further, in the above steps, the edge part of the detection image away from the center of the detection image should be selected. Due to digestive tract peristalsis, the transparent enclosure of the imaging system usually contacts with the inner wall of the digestive tract at its edge part. Therefore, the contact region is usually formed at the edge port of the detection image. Specifically, the step "selecting the edge part of the detection image away from the center of the detection image" comprises:

marking an inner ring on the detection image that is centered on the center of the detection image, and the inner ring is close to the edge of the detection image and does not intersect;

marking an outer ring on the detection image that is centered on the center of the detection image, and the outer ring intersects with the edge of the detection image;

recording the part enclosed by the inner ring, the outer ring, and the image edge as the edge part.

Therefore, the range of the edge part can be determined, and the range cannot be too large, causing difficulty in determination of the threshold τ, nor too small, causing difficulty in selecting the reference point P. The radius of the inner ring and the outer ring is determined by the size of the detection image.

As described above, during calibration, to ensure image accuracy, after each image is obtained, a radial distortion correction for the image is required. Therefore, in the specific implementation process of the present invention, a radial distortion correction is also required for the captured images. Specifically, the step "capturing and obtaining a detection image" comprises:

controlling the imaging system to capture and obtain an image;

correcting the radial distortion of the captured image and forming a detection image, and recording it as:

$$\mathrm{img\_out}(x,y) = \mathrm{img\_in}(x(1+l_1 R^2 + l_2 R^4), y(1+l_1 R^2 + l_2 R^4)) \quad (7);$$

where, $R = \sqrt{x^2 + y^2}$ represents the pixel distance from the pixel to the center of the detection image, $l_1$ and $l_2$ represent distortion parameters of the imaging system, x represents x-coordinate of the pixel, y represents y-coordinate of the pixel, img_in represents input image, and img_out represent corrected image.

Therefore, after correcting the radial distortion of the captured image, the detection image is obtained, and then an edge part is selected on the detection image to obtain the contact region and the reference point P.

Figure 3:
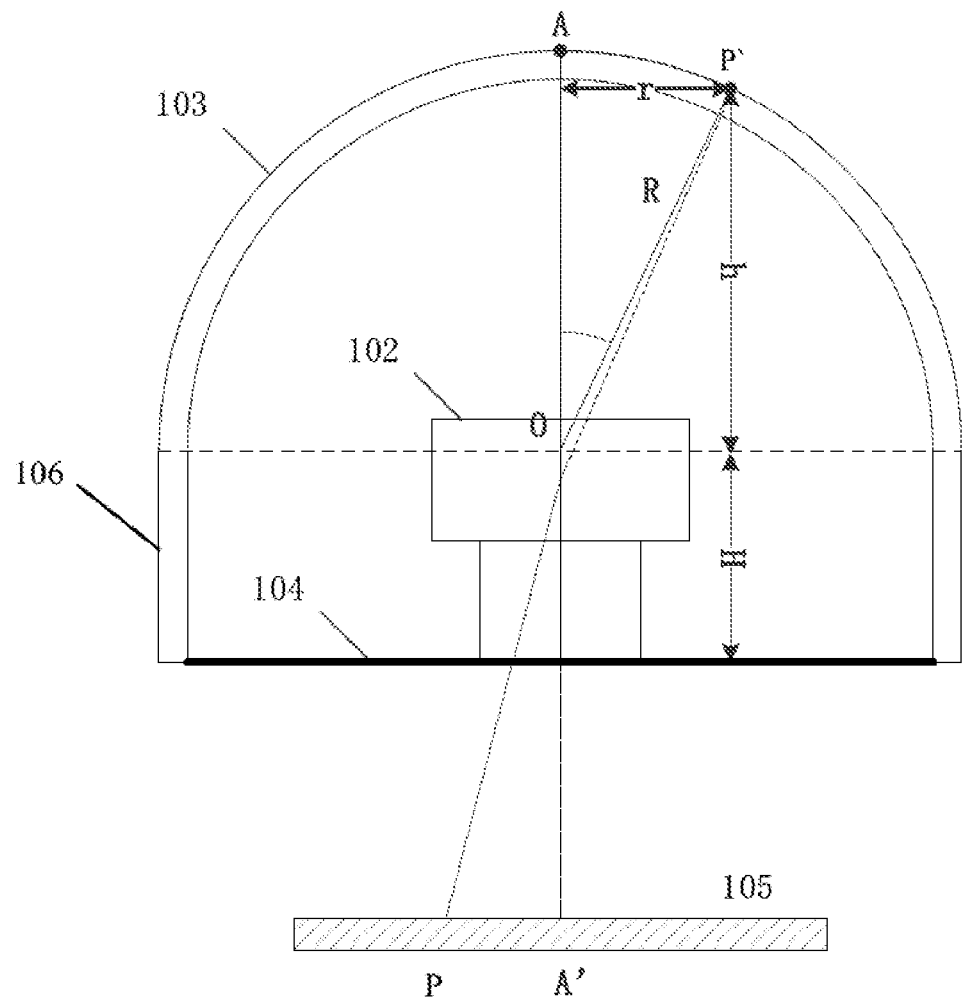
FIG. 3 shows a structural diagram of a partial structure of an imaging system according to the present invention.

Further, as shown in FIG. 3, after a reference point P is obtained, the relative angle θ between the reference point and the optical axis of the photographing unit 102 can be obtained in the calibration stage. Specifically, as shown in FIG. 3, the transparent enclosure comprises a front enclosure 103 and an annual enclosure 106 connecting the front enclosure 103 to the board 104, where a vertex of the front enclosure 103 is located on the optical axis of the photographing unit 102. Then, point A is designated as the vertex of the front enclosure 103, and the imaging point A' of the point A in the captured image is the center of the image. The target point P' is also on the front enclosure 103, and the target point P' forms a reference point P in the detection image 105. Point O is the spherical center of the front enclosure 103. It is known that the radius R of the front enclosure 103 and the axial length H of the annular enclosure 106, the relative angle θ between the reference point and the optical axis of the photographing unit 102 is the acute angle between the line connecting the reference point and the spherical center of the front enclosure 103 and the optical axis of the photographing unit 102. That is, θ=∠AOP'. The step "calculating the actual distance from the target point P' to the board 104 separately and recording it as depth distance $z_i$ of the reference point P" comprises:

obtaining the radius R of the front enclosure 103 of the transparent enclosure; calculating the depth distance R cos θ from the target point P' to the spherical center of the front enclosure 103 separately;

obtaining the axial length H of the annular enclosure of the transparent enclosure; calculating the depth distance $z_i = R \cos θ + H$ from the target point P' to the board 104 separately.

The coordinates of the target point P' in the z-axis direction is R cos θ+H.

Further, to facilitate subsequent calculation in detail, the actual coordinates of the target point P' in the xoy plane can also be calculated. Specifically, the distance between the target point P' and the point A in the xoy plane is R sin θ.

Figure 4:
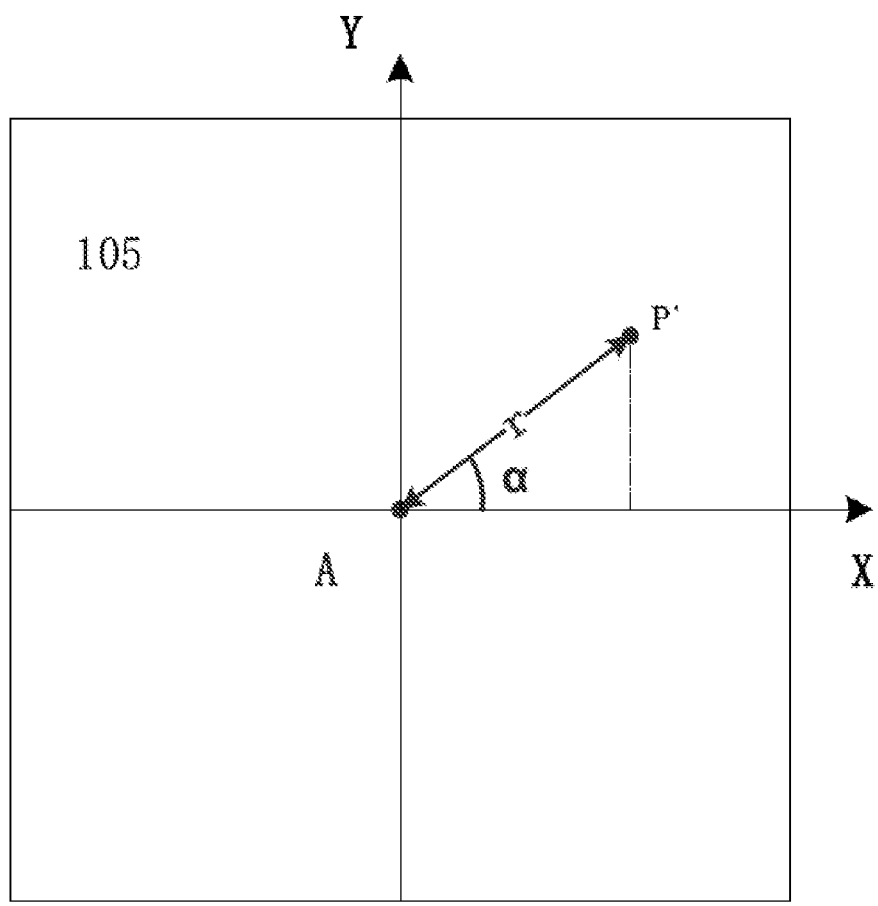
FIG. 4 shows a schematic diagram of an image captured by the imaging system according to the present invention.

Referring to FIG. 4, since point A' is the center of the image, point A is set as the origin of the coordinate system of xoy plane, and it is assumed that the angle between the target point P' and the origin A is α. Then, as described above, the actual coordinates of the target point P' in the xoy plane are: x=R sin θ cos α; y=R sin θ sin α. Then, the actual three-dimensional coordinates of the target point P' are (R sin θ cos α, R sin θ sin α, R cos θ+H). After the actual three-dimensional coordinates of the target point P' are obtained, the correction factors and the depth distance from the actual position of other pixels in the digestive tract to the board 104 can be obtained.

However, even if the depth distance from the actual position of each pixel in the digestive tract to the board 104 is obtained, if the object is too far from the capsule endoscope, the captured image can be too dark, and a large error can be easily caused in the depth distance z calculated according to the image brightness in equation 2; moreover, the image may be blurred with reduced resolution and larger noise, and the calculation error of the depth distance z becomes greater. Therefore, an effective section of the detection image must be defined, and only the detection image within the effective section can be used for measurement and calculation.

Therefore, after obtaining the depth distance or the depth image, it is necessary to compare the depth distance z. Specifically, the step "obtaining the depth distance from the actual position of each pixel in digestive tract to the board 104" or "integrating to obtain the actual three-dimensional coordinates $(S_i', z(x,y))$ of each pixel" further comprises:

determining the value of the depth distance z of each pixel;

when $t_1 \leq z \leq t_2$, it is determined that the pixel is within the effective section of the detection image;

when $z < t_1$ or $z > t_2$, it is determined that the pixel is within the ineffective section of the detection image.

where, $t_1 = 0$, and $t_2 = 60$ mm.

Therefore, after the final step "calculating or measuring the distance between any two pixels in the detection image or the area within any range", any two pixels or any range taken are also within the effective section of the detection image.

Specifically, in a first interaction mode, a straight-line distance between any two pixels selected by a user in the effective section can be calculated according to the three-dimensional coordinates of the two pixels.

Or, in a second interaction mode, a three-dimensional image of any region can be built according to the three-dimensional coordinates of pixels in the region selected by a user in the effective section, and a straight-line distance between any two pixels selected by the user from the three-dimensional image can be calculated.

Or, in a third interaction mode, the area of any region selected by a user in the effective section can be calculated according to the three-dimensional coordinates of the region.

Or, in a fourth interaction mode, a scale is formed in the effective section, and the graduations on the scale are marked as those of actual length, users can place the scale at different positions, and the graduations of the scale at different positions are also different, then users can read and measure by themselves.

Or, in a fifth interaction mode, the lesion region in the effective section can be automatically identified, with the size or area of the region calculated.

The above step "calculating the distance between any two pixels in the detection image or the area within any range"

is not limited to have only the five interaction modes, but the calculation method is based on that the actual three-dimensional coordinates of each pixel have been obtained, so other interaction modes are also within the protection scope of the present invention.

Therefore, accordingly, the present invention further provides a measuring system for objects in the digestive tract based on an imaging system, comprising: an identification module, configured to identify the contact region and the reference point P; a calibration calculation module, configured to calculate the relationship between the relative angle θ of the calibration point Q' relative to the optical axis of the photographing unit and the pixel distance Δq' from the imaging point Q to the center of the calibration image and record as equation 1, and to calculate the relationship between the brightness φ of any pixel in the calibration image and the depth distance z from the actual position of the pixel in the simulated digestive tract to the imaging system, and record it as equation 2, and to calculate and determine the relationship between the scale r of any pixel in the calibration image and the depth distance z from the actual position of the pixel in the simulated digestive tract to the imaging system, and record it as equation 3; a brightness detection module, configured to identify the brightness of any pixel or all pixels in the calibration image or the detection image; a measurement calculation module, configured to obtain the equation 1 of the calibration calculation module and the pixel distance Δp from the reference point P to the center of the detection image to calculate the relative angle θ of the target point P' relative to the optical axis of the photographing unit 102, and to calculate actual distance from the target point P' to the board and record it as depth distance $z_i$, and to obtain the depth distance $z_i$, the equation 2 of the calibration calculation module and the actual pixel brightness of the reference point P to calculate the correction factor $k_i$, and to obtain the equation 2 to calculate and obtain the depth distance z(x, y) from the actual position of each pixel in the digestive tract to the board, and to obtain the equation 3 to calculate the actual two-dimensional coordinates $S_i'$, and integrate to obtain the actual three-dimensional coordinates of ($S_i'$, z(x, y)) of each pixel.

In summary, the method for measuring objects in the digestive tract based on the imaging system in the present invention can obtain some parameter information in advance through the calibration stage of the imaging system, and thereby facilitate the calculation in the measurement stage and avoid calculation error caused by equipment difference between imaging systems. Secondly, by the storage of correction factors $k_i$, after the storage amount of $k_i$ is getting larger and the value of $k_i$ is getting more stable, the correction factor $k_i$ may not be calculated in the subsequent photographing process, so the use of a distance measuring unit can be ignored. Moreover, by determining the contact region, the reference point in the captured image can directly correspond to the target point on the transparent enclosure of the imaging system, so that no other hardware is needed to measure the depth distance $z_i$ for reference point, making the components simpler and the calculation steps more concise.

Finally, through separate measurement in different digestive tract environments in the calibration stage, different processing methods can be selected for different digestive tract environments to improve accuracy.

It should be understood that, although the specification is described in terms of embodiments, not every embodiment merely comprises an independent technical solution. Those skilled in the art should have the specification as a whole, and the technical solutions in each embodiment may also be combined as appropriate to form other embodiments that can be understood by those skilled in the art.

The present invention by no means is limited to the preferred embodiments described above. On the contrary, many modifications and variations are possible within the scope of the appended claims.

What is claimed is:

1. A method for measuring objects in a digestive tract based on an imaging system, comprising:
   simulating an environment in the digestive tract and starting a calibration process of the imaging system; said calibration process, comprising
   setting a plurality of calibration points Q' on a transparent enclosure of the imaging system;
   controlling a photographing unit of the imaging system to photograph and form a calibration image, and recording the calibration point Q' imaged in the calibration image as an imaging point Q;
   calculating and determining a relationship between a relative angle θ of the calibration point Q' relative to the optical axis of the photographing unit and a pixel distance Δq' from the imaging point Q to the center of the calibration image, and recording it as:

$$\theta = f(\Delta q') \quad (1);$$

calculating and determining a relationship between a brightness φ of any pixel in the calibration image and a depth distance z from an actual position of the pixel in the simulated digestive tract to a board where the photographing unit is disposed, and recording it as:

$$z(x,y) = g(\varphi(x,y)) \quad (2);$$

calculating a relationship between a scale r of any pixel in the calibration image and the depth distance z from the actual position of the pixel in the simulated digestive tract to the board where the photographing unit is disposed, where scale is the actual length represented by unit pixel in the image, and recording it as:

$$r = dz \quad (3);$$

performing a measurement process after the calibration process is completed; said measurement process, comprising
   placing the imaging system in the digestive tract;
   capturing and obtaining a detection image;
   determining a region in the detection image where the transparent enclosure contacts with the digestive tract wall, and recording it as a contact region, and setting at least one reference point P in the contact region, and recording the actual position of the reference point in the digestive tract as a target point P';
   calculating a pixel distance Δp from the reference point P to the center of the detection image separately, and putting it into equation 1 to obtain a relative angle θ of the target point P' relative to the optical axis of the photographing unit;
   calculating an actual distance from the target point P' to the board separately and recording it as depth distance $z_i$;
   obtaining a predicted brightness $g^{-1}(z_i)$ of the reference point P in the detection image according to equation 2 and the depth distance $z_i$;
   comparing the predicted brightness $g^{-1}(z_i)$ of the reference point P with an actual pixel brightness img($P_i$) of the reference point P to obtain a correction factor $k_i$, and recording it as:

$$k_i = \frac{g^{-1}(z_i)}{\text{img}(P_i)}; \qquad (4)$$

obtaining a mean value $\bar{k}$ of the correction factors $k_i$ of all reference points P;

calibrating all pixels in the detection image with the mean value $\bar{k}$ of the correction factors to obtain a depth distance from an actual position of each pixel in the digestive tract to the board, and recording it as depth image z(x, y), where:

$$z(x,y)=g(\bar{k}\text{img}(x,y)) \qquad (5);$$

calculating a scale r of each pixel in the detection image according to equation 3 and the depth image z(x, y);

obtaining pixel coordinates $S_i$ of each pixel point in the detection image, and calculating the actual two-dimensional coordinates $S_i'$ of each pixel in the detection image by the scale r;

integrating to obtain actual three-dimensional coordinates ($S_i'$, z(x, y)) of each pixel;

calculating or measuring a distance between any two pixels in the detection image or the area within any range;

wherein a photographing unit enclosed in the transparent enclosure, placed in between a board and a front end of the transparent enclosure;

the transparent enclosure is configured to be placed in the digestive tract and form the contact region;

and the image system comprises one or more computer processors to calibrate and calculate.

2. The method of claim 1, wherein the step "determining the region in the detection image where the transparent enclosure contacts with the digestive tract wall" comprises:

selecting an edge part of the detection image away from the center of the detection image;

obtaining a brightness T of each pixel in the edge part;

gathering pixels in a region which the brightness T is greater than a threshold τ as the contact region.

3. The method of claim 2, wherein the step "selecting the edge part of the detection image away from the center of the detection image" comprises:

marking an inner ring on the detection image that is centered on the center of the detection image, wherein the inner ring is close to the edge of the detection image and does not intersect;

marking an outer ring on the detection image that is centered on the center of the detection image, wherein the outer ring intersects with the edge of the detection image; and recording the part enclosed by the inner ring, the outer ring, and the image edge as the edge part.

4. The method of claim 1, wherein the digestive tract comprises a plurality of regions and the imaging system comprises a plurality of exposure levels, and wherein, after the step "obtaining the mean value $\bar{k}$ of the correction factors $k_i$ of all reference points P", the correction factors are stored according to different exposure levels and different digestive tract regions.

5. The method of claim 4, wherein after two or more mean values $\bar{k}$ of correction factors are obtained at the same exposure level and digestive tract region, the average of the mean values $\bar{k}$ of correction factors is calculated before storing and updating.

6. The method of claim 1, wherein the step "calculating the actual distance from the target point P' to the board separately and recording it as depth distance $z_i$ of the reference point P'" comprises:

obtaining the radius R of a front enclosure of the transparent enclosure;

calculating a distance R cos θ from the target point P' to the spherical center of the front enclosure separately;

obtaining the axial length H of an annular enclosure of the transparent enclosure;

calculating the depth distance $z_i$=R cos θ+H from the target point P' to the board separately.

7. The method of claim 1, wherein the step "obtaining the depth distance from the actual position of each pixel in the digestive tract to the board" or "integrating to obtain the actual three-dimensional coordinates ($S_i'$,z(x,y)) of each pixel" further comprises:

determining a value of the depth distance z of each pixel;

when $t_1 \leq z \leq t_2$, it is determined that the pixel is within an effective section of the detection image;

when $z<t_1$ or $z>t_2$, it is determined that the pixel is within an ineffective section of the detection image.

8. The method of claim 7, wherein the step "calculating or measuring the distance between any two pixels in the detection image or the area within any range" is followed by:

calculating a straight-line distance between any two pixels selected by a user in the effective section according to the three-dimensional coordinates of the two pixels; or, building a three-dimensional image of any area according to the three-dimensional coordinates of pixels in the area selected by a user in the effective section, and calculating a straight-line distance between any two pixels selected by the user from the three-dimensional image; or, calculating the area of any region selected by a user in the effective section according to the three-dimensional coordinates of the region; or, forming a scale in the effective section, and marking graduations on the scale as those of actual length; or, identifying the lesion region in the effective section automatically, and calculating the size or area of the region.

9. The method of claim 7, wherein $t_1$=0, and $t_2$=60 mm.

10. The method of claim 1, wherein the step "capturing and obtaining a detection image" comprises:

controlling the imaging system to capture and obtain an image;

correcting a radial distortion of the captured image and forming a detection image, and recording it as:

$$\text{img\_out}(x,y)=\text{img\_in}(x(1+l_1R^2+l_2R^4),y(1+l_1R^2+l_2R^4)) \qquad (6);$$

where, $R=\sqrt{x^2+y^2}$ represents the pixel distance from the pixel to the center of the detection image, $l_1$ and $l_2$ represent distortion parameters of the imaging system, x represents x-coordinate of the pixel, y represents y-coordinate of the pixel, img_in represents input image, and img_out represent corrected image.

11. A measuring system for objects in digestive tract based on an imaging system, comprising:

one or more computer processors configured:

to identify a contact region and a reference point P;

to calculate the relationship between a relative angle θ of a calibration point Q' relative to an optical axis of a photographing unit of the imaging system and a pixel distance Δq' from an imaging point Q to a center of a calibration image and record as equation 1, and to calculate a relationship between a brightness φ of any pixel in the calibration image and the depth distance z from the actual position of the pixel in a simulated digestive tract to the imaging system, and record it as equation 2, and to calculate and determine the relationship between a scale r of any pixel in the calibration image and the depth distance z from the actual position of the pixel in the simulated digestive tract to the imaging system, and record it as equation 3;

$$\theta = f(\Delta q') \quad (1);$$

$$z(x,y) = g(\varphi(x,y)) \quad (2);$$

$$r = dz \quad (3);$$

to identify the brightness of any pixel or all pixels in the calibration image or a detection image;

to obtain equation 1 and the pixel distance $\Delta p$ from the reference point P to the center of the detection image to calculate the relative angle $\theta$ of a target point P' relative to the optical axis of the photographing unit, and to calculate actual distance from the target point P' to a board where the photographing unit is disposed and record it as depth distance $z_i$, and to obtain the depth distance $z_i$, equation 2 and the actual pixel brightness of the reference point P to calculate a correction factor $k_i$, and to obtain equation 2 to calculate and obtain the depth distance $z(x, y)$ from the actual position of each pixel in the digestive tract to the board, and to obtain equation 3 to calculate the actual two-dimensional coordinates $S_i'$, and integrate to obtain the actual three-dimensional coordinates of $(S_i', z(x, y))$ of each pixel.

* * * * *